US012302206B2

(12) United States Patent
Decrop et al.

(10) Patent No.: US 12,302,206 B2
(45) Date of Patent: May 13, 2025

(54) PREVENTATIVE WORKPLACE INJURY ALERTING SYSTEM UTILIZING MMWAVE 5G POSITIONAL LOCALIZATION

(71) Applicant: International Business Machines Corporation, Armonk, NY (US)

(72) Inventors: Clement Decrop, Arlington, VA (US); Michael Bender, Rye Brook, NY (US); Hernan A. Cunico, Holly Springs, NC (US); Martin G. Keen, Cary, NC (US)

(73) Assignee: International Business Machines Corporation, Armonk, NY (US)

( * ) Notice: Subject to any disclaimer, the term of this patent is extended or adjusted under 35 U.S.C. 154(b) by 643 days.

(21) Appl. No.: 17/643,033

(22) Filed: Dec. 7, 2021

(65) Prior Publication Data
US 2023/0179983 A1    Jun. 8, 2023

(51) Int. Cl.
A61B 5/11 (2006.01)
H04W 4/029 (2018.01)
H04W 4/38 (2018.01)
H04W 4/90 (2018.01)

(52) U.S. Cl.
CPC ............ H04W 4/90 (2018.02); A61B 5/1116 (2013.01); H04W 4/029 (2018.02); H04W 4/38 (2018.02)

(58) Field of Classification Search
CPC ........ H04W 4/90; H04W 4/029; H04W 4/38; H04W 4/025; G16H 40/63; G16H 50/30; A61B 5/7264; A61B 5/7275; A61B 5/7282; A61B 5/1117; A61B 5/1128; A61B 5/746; A61B 5/1114; A61B 2503/20; A61B 5/1116
See application file for complete search history.

(56) References Cited

U.S. PATENT DOCUMENTS 9,844,344 B2  12/2017  Horseman
9,866,673 B2   1/2018  Gabel
(Continued)

FOREIGN PATENT DOCUMENTS

CN  108983225 A  12/2018
CN  109196925 A   1/2019
EP    3772396 A1   2/2021
(Continued)

OTHER PUBLICATIONS

Bartoletti et al., "5G Localization and Context-Awareness", 5G Italy, 2018, 22 Pages.
(Continued)

Primary Examiner — Marcos L Torres
(74) Attorney, Agent, or Firm — Joseph P. Curcuru

(57) ABSTRACT

In an approach for monitoring a user's in-flight activity and/or a pattern of movement of a user and warning the user of an in-flight activity or a pattern of movement that could lead to a potential short-term or long-term injury, a processor monitors a body movement and a posture of a user through an application of micro-location analysis enabled by a mesh network of 5G sensors over a period of time. A processor determines whether the body movement and the posture detected can lead to an activity or a series of activities that can result in a potential injury. Responsive to determining a pre-set threshold of risk has been reached, a processor issues a real time alert to the user to warn of the potential injury.

20 Claims, 4 Drawing Sheets

(56) References Cited

U.S. PATENT DOCUMENTS 10,123,751 B2 * 11/2018 Petterson .............. A61B 5/7405
11,803,955 B1 * 10/2023 Pandya ................ G08B 29/186

FOREIGN PATENT DOCUMENTS

WO       2019078955 A1    4/2019
WO       2020028986 A1    2/2020

OTHER PUBLICATIONS

Boland, Mike, "How Will 5G Unlock Location Targeting?", Street Fight Magazine, Mar. 20, 2019, 6 Pages.

Murphy et al., "An upper body garment with integrated sensors for people with neurological disorders-early development and evaluation", BMC Biomedical Engineering, vol. 1, Article No. 3, 2019, 13 Pages.

National Safety Council, "Workplace Injuries by the Numbers", National Safety Council, 2021, 2 Pages.

Kiang et al., "PoseCNN: A Convolutional Neural Network for 6D Object Pose Estimation in Cluttered Scenes", arXiv: 1711.00199v3 [cs.CV], May 26, 2018, 10 Pages.

* cited by examiner

PREVENTATIVE WORKPLACE INJURY ALERTING SYSTEM UTILIZING MMWAVE 5G POSITIONAL LOCALIZATION

BACKGROUND OF THE INVENTION

The present invention relates generally to the field of data processing, and more particularly to a preventative workplace injury alerting system utilizing mmWave 5G positional localization.

Wearable technology devices, also referred to as "wearables," are a category of smart electronic devices that can detect, analyze, and transmit information concerning the wearer's body (e.g., vital signs and ambient data) and, in some cases, allow immediate biofeedback to the wearer. Wearable technology devices can be worn as an accessory, embedded in a clothing item, implanted in a body, or even tattooed on the skin. Wearable technology devices are hands-free devices with practical uses, powered by microprocessors and enhanced with the ability to send and receive data via the internet. The growth of mobile networks enabled the development of wearable technology devices. Fitness activity trackers were the first big wave of wearable technology devices to catch on with consumers. Then, the wristwatch became a screen and more robust mobile applications were added. Bluetooth headsets, smartwatches, and web-enabled glasses all allow people to receive data via the internet. The gaming industry added to the wearable technology devices, with virtual reality and augmented reality headsets.

Neural networks can provide additional data to supplement the data received from wearable technology devices. Neural networks are a subset of machine learning and are at the heart of deep learning algorithms. Neural networks are comprised of node layers, containing an input layer, one or more hidden layers, and an output layer. Each node connects to another and has an associated weight and threshold. If the output of any individual node is above the specified threshold value, that node is activated, sending data to the next layer of the network. Otherwise, no data is passed along to the next layer of the network. A convolutional neural network (CNN) is a type of neural network used in image recognition and computer processing tasks specifically designed to process pixel data. CNNs provide a scalable approach to image classification and object recognition tasks, leveraging principles from linear algebra, specifically matrix multiplication, to identify patterns within an image.

The data collected from wearable technology devices and neural networks can be reported to a 5G network. The 5G network is the fifth generation of wireless networking technology. There are currently 340 million 5G network connections. By 2025, it is predicted that there will be more than 1.7 billion 5G network connections worldwide. Like its predecessor, the 4G network, the 5G network is a cellular network, in which the service area is divided into small geographical areas called cells. All 5G wireless devices in a cell are connected to the Internet and telephone network by radio waves through a local antenna in the cell. However, the 5G network differs from the 4G network in fundamental topology. Instead of large cell towers, the 5G network consists of smaller and far more frequently clustered 5G stations that blanket areas forming a type of edge-computing mesh network. The 5G mesh network utilizes millimeter wave (mmWAVE) signals to provide microlocation capabilities. This brings about significant advances in positional localization. Whereas Global Navigation Satellite System (GNSS) is accurate to 2-3 meters, a mmWAVE 5G positional localization system is accurate at the centimeter level. Additionally, unlike GNSS solutions, the mmWAVE 5G positional localization is equally accurate indoors and outdoors.

From the data collected from wearable technology devices and neural networks and reported to the 5G network, the six degrees of freedom (6D Positioning) can be derived. The 6D Positioning refers to the specific number of axes that a rigid body can freely move in a three-dimensional space. Specifically, the rigid body can freely move in three dimensions (i.e., horizontal, vertical, and depth), on the X, Y, and Z axes. The rigid body can also change orientation between those axes through rotation called pitch, yaw, and roll. 6D Positioning provides X, Y, and Z and pitch, yaw, and roll, whereas three degrees provides X, Y, and Z only.

SUMMARY

Aspects of an embodiment of the present invention disclose a method, computer program product, and computer system for monitoring a user's in-flight activity and/or a pattern of movement of a user and warning the user of an in-flight activity or a pattern of movement that could lead to a potential short-term or long-term injury, a processor monitors a body movement and a posture of a user through an application of micro-location analysis enabled by a mesh network of 5G sensors over a period of time. A processor determines whether the body movement and the posture detected can lead to an activity or a series of activities that can result in a potential injury. Responsive to determining a pre-set threshold of risk has been reached, a processor issues a real time alert to the user to warn of the potential injury.

In some aspects of an embodiment of the present invention, a processor gathers sensor data on the body movement and the posture of the user from a user computing device. A processor captures one or more photographs of the body movement and the posture of the user through a camera. A processor gathers position data from the one or more photographs of the body movement and the posture using a convolutional neural network.

In some aspects of an embodiment of the present invention, a processor derives a three-dimensional position in space of the user from the sensor data and the position data. A processor derives a three-dimensional orientation of the user from the sensor data and the position data. A processor derives a six-dimensional position of the user from the three-dimensional position in space and the three-dimensional orientation of the user. A processor analyzes the six-dimensional position of the user to derive an in-flight activity and a pattern of movement of the user. A processor compares the in-flight activity and the pattern of movement of the user to one or more prior instances of in-flight activities and patterns of movement. A processor performs an outcome analysis on the in-flight activity and the pattern of movement of the user based on a comparison. A processor calculates a score of the in-flight activity and the pattern of movement of the user based on the likelihood that the in-flight activity and the pattern of movement could lead to the potential injury. A processor categorizes the in-flight activity and the pattern of movement of the user based on a risk of an immediate potential injury or a long term potential injury. A processor determines whether the pre-set threshold of risk has been reached based on the score of the in-flight activity and the pattern of movement of the user.

In some aspects of an embodiment of the present invention, a processor calculates one or more possible paths of the user. A processor determines the one or more possible paths of the user are within a threshold of one or more historical paths. A processor predicts a possibility the potential injury will occur.

In some aspects of an embodiment of the present invention, a processor analyzes a medical history of the user. A processor performs a situational analysis of the in-flight activity and the pattern of movement of the user.

In some aspects of an embodiment of the present invention, the real time alert includes the in-flight activity and the pattern of movement of the user, the potential injury, and a recommended posture to perform the in-flight activity and the pattern of movement of the user.

In some aspects of an embodiment of the present invention, the real time alert is issued based on a level of risk of the in-flight activity and the pattern of movement of the user.

In some aspects of an embodiment of the present invention, the level of risk is determined based on the score calculated of the in-flight activity and the pattern of movement of the user.

In some aspects of an embodiment of the present invention, the level of risk is a high-risk situation, a medium-risk situation, or a low-risk situation; in the high-risk situation, the real time alert is issued through a myriad of notification methods including an alarm, a buzzing, and a haptic feedback alert sent to the user and to one or more people in direct proximity of the user; in the medium-risk situation, the real time alert is issued through a myriad of less aggressive notification methods including an alarm sounding at a lower volume, a buzz that is less prolonged, and a haptic feedback alert sent to the user; and in the low-risk situation, the real time alert is issued through a casual notification method such as a ping sent to the user.

These and other features and advantages of the present invention will be described in, or will become apparent to those of ordinary skill in the art in view of, the following detailed description of the example embodiments of the present invention.

DETAILED DESCRIPTION

Figure 1:
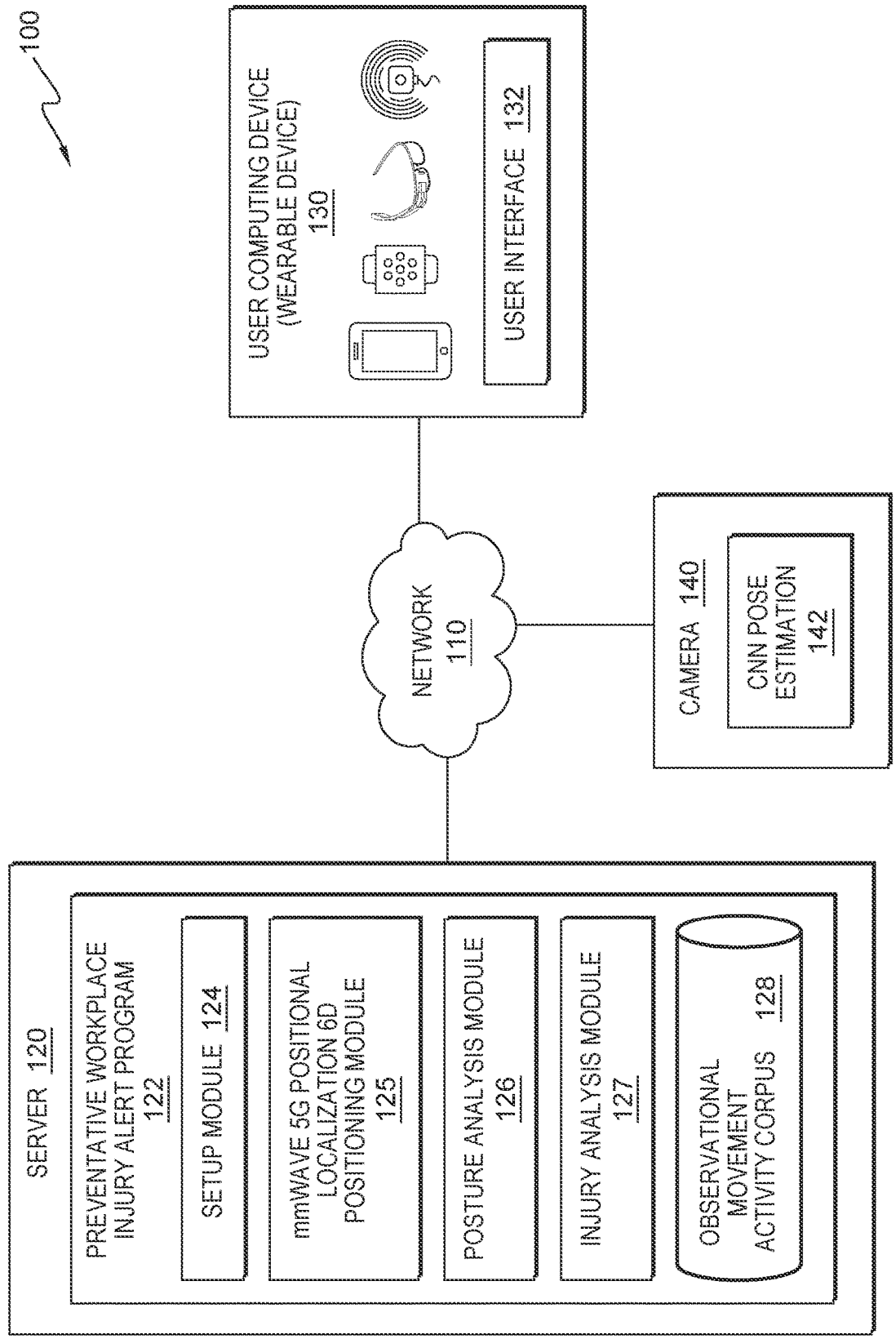
FIG. 1 is a block diagram illustrating a distributed data processing environment, in accordance with an embodiment of the present invention.

Embodiments of the present invention recognize that work and hazards related to work can result in workplace injuries and compromise the health and safety of workers. According to the U.S. Bureau of Labor Statistics, an estimated 2.8 million nonfatal workplace injuries occurred in private companies in the United States in the year 2019. Consequently, 70 million production days were lost. Overexertion and bodily reaction, slips, trips, falls, and contact with objects and equipment are the highest causes of workplace injuries and make up nearly 84% of the estimated 2.8 million nonfatal workplace injuries.

Embodiments of the present invention recognize that the risk of a workplace injury increased as the work requirements for excessive physical effort, lifting heavy loads, and stooping, kneeling, and/or crouching increased. Specifically, the risk of a workplace injury among those whose work had these physical work requirements "all or almost all the time" was two-times that of those whose work did not have such requirements. Evidence has shown that heavy physical work, lifting and forceful movements, bending and twisting, whole-body vibration, and static work postures are associated with back injuries. Evidence has also shown that repetition, force, and posture are associated with neck and shoulder injuries.

Embodiments of the present invention recognize that workplace injuries can be devastating for businesses, especially small businesses who have fewer workers available to take on new roles when another worker is on leave. Embodiments of the present invention recognize that the best way to minimize workplace injuries is to prevent workplace injuries from happening in the first place. Therefore, embodiments of the present invention recognize the need for a preventative workplace injury alert program.

Embodiments of the present invention provide a system and method to gather sensor data on the movement and the posture of a body of a worker (hereinafter referred to as a user) from user computing device 130 and position data from one or more photographs taken of the user using Convolutional Neural Network (CNN) pose estimation 142; to derive the precise 6D position of the user's body or the user's body part from the sensor data and the position data; to derive the user's in-flight activity and the user's pattern of movement from the 6D position of the user's body or the user's body part; to produce a personalized and aggregate movement outcome analysis and posture analysis as well as an analyzed exertion outcome detailing the potential results of a workplace injury because of the user's in-flight activity and/or the user's pattern of movement; and to issue a real time alert to warn the user of an in-flight activity or a pattern of movement that could lead to a potential short-term or long-term injury.

Implementation of embodiments of the present invention may take a variety of forms, and exemplary implementation details are discussed subsequently with reference to the Figures.

FIG. 1 is a block diagram illustrating a distributed data processing environment, generally designated 100, in accordance with an embodiment of the present invention. In the depicted embodiment, distributed data processing environment 100 includes server 120, user computing device 130, and camera 140, interconnected over network 110. Distributed data processing environment 100 may include additional servers, computers, computing devices, IoT sensors, and other devices not shown. The term "distributed" as used herein describes a computer system that includes multiple, physically distinct devices that operate together as a single computer system. FIG. 1 provides only an illustration of one embodiment of the present invention and does not imply any limitations with regards to the environments in which different embodiments may be implemented. Many modifications to the depicted environment may be made by those skilled in the art without departing from the scope of the invention as recited by the claims.

Network 110 operates as a computing network that can be, for example, a telecommunications network, a local area network (LAN), a wide area network (WAN), such as the Internet, or a combination of the three, and can include wired, wireless, or fiber optic connections. Network 110 can include one or more wired and/or wireless networks capable of receiving and transmitting data, voice, and/or video signals, including multimedia signals that include data, voice, and video information. In general, network 110 can be any combination of connections and protocols that will support communications between server 120, user computing device 130, camera 140, and other computing devices (not shown) within distributed data processing environment 100.

Server 120 operates to run preventative workplace injury alert program 122 and to send and/or store data in observational movement activity corpus 128. In an embodiment, server 120 can send data from observational movement activity corpus 128 to user computing device 130. In an embodiment, server 120 can receive data in observational movement activity corpus 128 from user computing device 130. In one or more embodiments, server 120 can be a standalone computing device, a management server, a web server, a mobile computing device, or any other electronic device or computing system capable of receiving, sending, and processing data and capable of communicating with user computing device 130 via network 110. In one or more embodiments, server 120 can be a computing system utilizing clustered computers and components (e.g., database server computers, application server computers, etc.) that act as a single pool of seamless resources when accessed within distributed data processing environment 100, such as in a cloud computing environment. In one or more embodiments, server 120 can be a laptop computer, a tablet computer, a netbook computer, a personal computer, a desktop computer, a personal digital assistant, a smart phone, or any programmable electronic device capable of communicating with user computing device 130 and other computing devices (not shown) within distributed data processing environment 100 via network 110. Server 120 may include internal and external hardware components, as depicted and described in further detail in FIG. 4.

Preventative workplace injury alert program 122 operates to gather sensor data on the movement and the posture of a body of a user from user computing device 130 and position data from one or more photographs taken of the user using CNN pose estimation 142; to derive the precise 6D position of the user's body or the user's body part from the sensor data and the position data; to derive the user's in-flight activity and the user's pattern of movement from the 6D position of the user's body or the user's body part; to produce a personalized and aggregate movement outcome analysis and posture analysis as well as an analyzed exertion outcome detailing the potential results of a workplace injury because of the user's in-flight activity and/or the user's pattern of movement; and to issue a real time alert to warn the user of an in-flight activity or a pattern of movement that could lead to a potential short-term or long-term injury. In the depicted embodiment, preventative workplace injury alert program 122 contains setup module 124, mmWAVE 5G positional localization 6D positioning module 125, posture analysis module 126, and injury analysis module 127.

Setup module 124 completes a one-time setup with a user. The one-time setup allows for setup module 124 to capture relevant information about the user to create a user profile and register a user computing device with preventative workplace injury alert program 122. mmWAVE 5G positional localization 6D positioning module 125 derives a 3D position in space, a 3D orientation, and a 6D position of the user's body from the sensor data and the position data gathered. mmWAVE 5G positional localization 6D positioning module 125 analyzes the 6D position of the user's body or the user's body part to derive the user's in-flight activity and pattern of movement. Posture analysis module 126 analyzes the user's in-flight activity to determine whether the user may experience problems over a longer period of time because of poor posture. Injury analysis module 127 calculates a score of the user's in-flight activity and pattern of movement based on the likelihood that the in-flight activity poses a risk of short- or long-term injury.

In the depicted embodiment, preventative workplace injury alert program 122 is a standalone program. In another embodiment, preventative workplace injury alert program 122 may be integrated into another software product, such as a safety management software. In the depicted embodiment, preventative workplace injury alert program 122 resides on server 120. In another embodiment, preventative workplace injury alert program 122 may reside on user computing device 130 or on another computing device (not shown), provided that preventative workplace injury alert program 122 has access to network 110.

In an embodiment, the user of user computing device 130 registers with server 120. For example, the user completes a registration process (e.g., user validation), provides information to create a user profile, and authorizes the collection, analysis, and distribution (i.e., opts-in) of relevant data on identified computing devices (e.g., on user computing device 130) by server 120 (e.g., via preventative workplace injury alert program 122). Relevant data includes, but is not limited to, personal information or data provided by the user or inadvertently provided by the user's device without the user's knowledge; tagged and/or recorded location information of the user (e.g., to infer context (i.e., time, place, and usage) of a location or existence); time stamped temporal information (e.g., to infer contextual reference points); and specifications pertaining to the software or hardware of the user's device. In an embodiment, the user opts-in or opts-out of certain categories of data collection. For example, the user can opt-in to provide all requested information, a subset of requested information, or no information. In one example scenario, the user opts-in to provide time-based information, but opts-out of providing location-based information (on all or a subset of computing devices associated with the user). In an embodiment, the user opts-in or opts-out of certain categories of data analysis. In an embodiment, the user opts-in or opts-out of certain categories of data distribution. Such preferences can be stored in observational movement activity corpus 128. The operational steps for setup module 124 of preventative workplace injury alert program 122 are depicted and described in further detail with respect to FIG. 2. The overall operational steps of preventative workplace injury alert program 122 are depicted and described in further detail with respect to FIG. 3.

Observational movement activity corpus 128 is a database. Observational movement activity corpus 128 operates as a repository for data received, used, and/or generated by preventative workplace injury alert program 122. A database is an organized collection of data. Data includes, but is not limited to, information about user preferences (e.g., general user system settings such as alert notifications for user computing device 130); information about alert notification preferences; sensor data on the movement and the posture of the user's body; position data from the one or more photographs of the user; a 3D position in space of the user's body or the user's body part; a 3D orientation of the user's body or the user's body part; identifying data of the user along with a 6D position of the user's body or the user's body part; a user's in-flight activity and/or the user's pattern of movement; prior instances of similar in-flight activities and/or patterns of movement; a real time alert issued; a report of near misses; and any other data received, used, and/or generated by preventative workplace injury alert program 122.

Observational movement activity corpus 128 can be implemented with any type of device capable of storing data and configuration files that can be accessed and utilized by server 120, such as a hard disk drive, a database server, or a flash memory. In an embodiment, observational movement activity corpus 128 is accessed by issue detection and resolution program 122 to store and/or to access the data. In the depicted embodiment, observational movement activity corpus 128 resides on server 120. In another embodiment, observational movement activity corpus 128 may reside on another computing device, server, cloud server, or spread across multiple devices elsewhere (not shown) within distributed data processing environment 100, provided that issue detection and resolution program 122 has access to observational movement activity corpus 128.

The present invention may contain various accessible data sources, such as observational movement activity corpus 128, that may include personal and/or confidential company data, content, or information the user wishes not to be processed. Processing refers to any operation, automated or unautomated, or set of operations such as collecting, recording, organizing, structuring, storing, adapting, altering, retrieving, consulting, using, disclosing by transmission, dissemination, or otherwise making available, combining, restricting, erasing, or destroying personal and/or confidential company data. Preventative workplace injury alert program 122 enables the authorized and secure processing of personal data.

Preventative workplace injury alert program 122 provides informed consent, with notice of the collection of personal and/or confidential data, allowing the user to opt-in or opt-out of processing personal and/or confidential data. Consent can take several forms. Opt-in consent can impose on the user to take an affirmative action before personal and/or confidential data is processed. Alternatively, opt-out consent can impose on the user to take an affirmative action to prevent the processing of personal and/or confidential data before personal and/or confidential data is processed. Preventative workplace injury alert program 122 provides information regarding personal and/or confidential data and the nature (e.g., type, scope, purpose, duration, etc.) of the processing. Preventative workplace injury alert program 122 provides the user with copies of stored personal and/or confidential company data. Preventative workplace injury alert program 122 allows the correction or completion of incorrect or incomplete personal and/or confidential data. Preventative workplace injury alert program 122 allows for the immediate deletion of personal and/or confidential data.

User computing device 130 operates to run user interface 132 through which a user can interact with preventative workplace injury alert program 122 on server 120. In an embodiment, user computing device 130 is a device that performs programmable instructions. For example, user computing device 130 may be an electronic device, such as a smart phone (i.e., a mobile device containing movement sensors such as an accelerometer and gyroscope to measure the overall movements of the body carrying the mobile device), a smart watch (i.e., a wearable technology device containing movement sensors such as an accelerometer and gyroscope to measure the movements of the arm wearing the wearable device), an augmented reality device (e.g., a pair of smart glasses containing sensors to track precise head movements), a garment integrated sensor (i.e., a sensor integrated into a piece of clothing to track various movements based upon the placement of the sensor, e.g., a sensor integrated into a shirt sleeve to track shoulder movement or a sensor integrated into a pair of pants near the waist band to track hip movement), or any programmable electronic device capable of running user interface 132 and of communicating (i.e., sending and receiving data) with preventative workplace injury alert program 122 via network 110. In general, user computing device 130 represents any programmable electronic device or a combination of programmable electronic devices capable of executing machine readable program instructions and communicating with other computing devices (not shown) within distributed data processing environment 100 via network 110. In the depicted embodiment, user computing device 130 includes an instance of user interface 132. User computing device 130 may include components as described in further detail in FIG. 4.

User interface 132 operates as a local user interface between preventative workplace injury alert program 122 on server 120 and a user of user computing device 130. In some embodiments, user interface 132 is a graphical user interface (GUI), a web user interface (WUI), and/or a voice user interface (VUI) that can display (i.e., visually) or present (i.e., audibly) text, documents, web browser windows, user options, application interfaces, and instructions for operations sent from preventative workplace injury alert program 122 to a user via network 110. User interface 132 can also display or present alerts including information (such as graphics, text, and/or sound) sent from preventative workplace injury alert program 122 to a user via network 110. In an embodiment, user interface 132 is capable of sending and receiving data (i.e., to and from preventative workplace injury alert program 122 via network 110, respectively). Through user interface 132, a user can opt-in to preventative workplace injury alert program 122; receive a request for information; input requested information; set user preferences and alert notification preferences; create a user profile; register user computing device 130; grant permission to preventative workplace injury alert program 122 to gather sensor data on the body movement and the posture of the user during a defined period of time through user computing device 130; receive a real time alert as an alert notification; and receive a report of near misses.

A user preference is a setting that can be customized for a particular user. A set of default user preferences are assigned to each user of preventative workplace injury alert program 122. A user preference editor can be used to update values to change the default user preferences. User preferences that can be customized include, but are not limited to, general user system settings, specific user profile settings, alert notification settings, and machine-learned data collection/storage settings.

Machine-learned data is a user's personalized corpus of data. Machine-learned data includes, but is not limited to, data regarding past results of iterations of issue detection and resolution program 122 and a user's previous response to an alert notification sent by customer conversation advancement program 122. Preventative workplace injury alert program 122 self-learns by tracking user activity, by classifying and retaining new content, and by improving with each iteration of preventative workplace injury alert program 122.

Preventative workplace injury alert program 122 classifies in-flight activities and patterns of movement based on the likelihood a user will perform the in-flight activity or pattern of movement. In an embodiment, preventative workplace injury alert program 122 classifies the in-flight activity or pattern of movement on a scale of 1 (i.e., a low chance the in-flight activity or pattern of movement will be performed) to 10 (i.e., a high chance the in-flight activity or pattern of movement will be performed). By classifying and retaining such data, preventative workplace injury alert program 122 can automatically filter out certain in-flight activities or patterns of movement over time and ensure that repetitive information is not generated and sent to the user. Instead, preventative workplace injury alert program 122 bypasses the repetitive information and locates new information for the user. Preventative workplace injury alert program 122 can also recommend suggestions (e.g., on the likelihood of performance of certain in-flight activities or patterns of movement) to the user so that the user can be aware of the potential short-term and long-term injuries caused by performing certain in-flight activities or patterns of movement.

Camera 140 operates to capture one or more photographs and/or videos of the user. CNN pose estimation 142 operates to gather position data from the one or more photographs and/or videos of the user. CNN pose estimation 142 is a convolutional neural network used in image recognition and computer processing tasks specifically designed to process pixel data. CNN pose estimation 142 provides a scalable approach to image classification and object recognition tasks, leveraging principles from linear algebra, specifically matrix multiplication, to identify patterns within an image.

Figure 2:
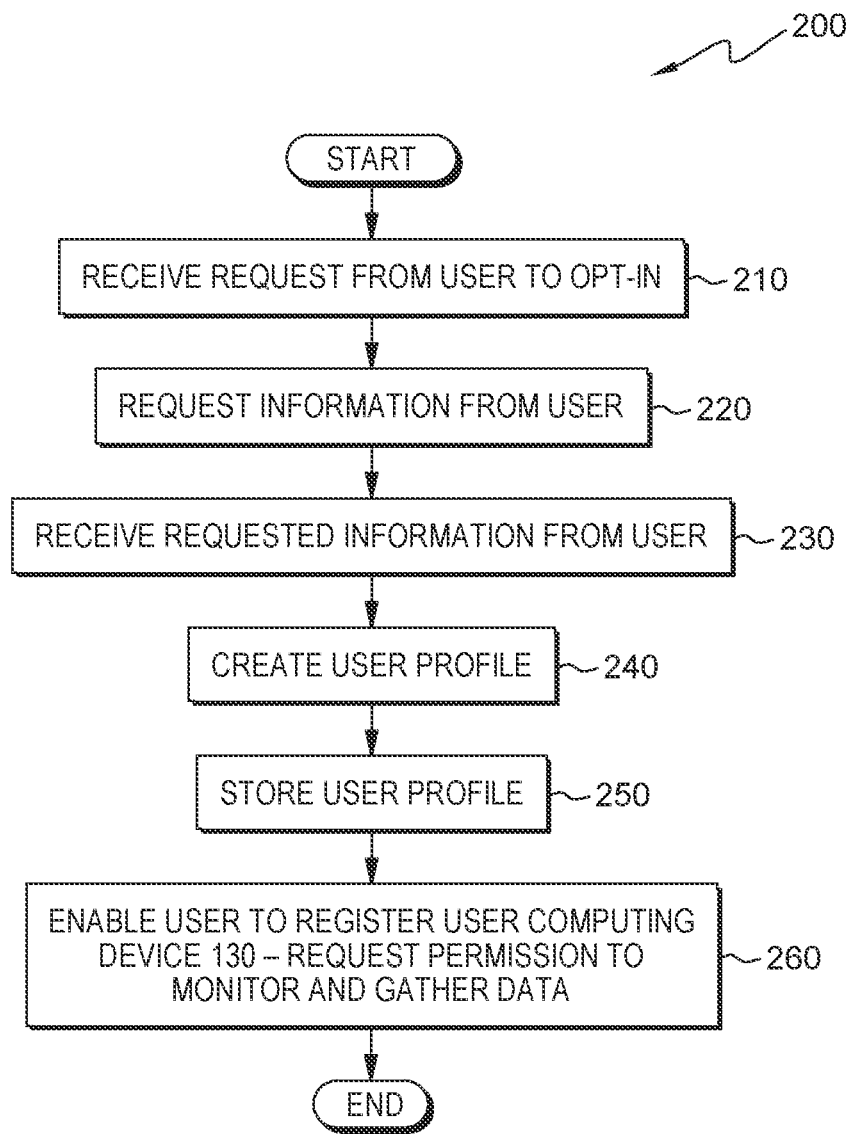
FIG. 2 is a flowchart illustrating the operational steps for a setup module of a preventative workplace injury alert program, on a server within the distributed data processing environment of FIG. 1, in accordance with an embodiment of the present invention.

FIG. 2 is a flowchart, generally designated 200, illustrating the operational steps for setup module 124 of preventative workplace injury alert program 122 on server 120 in distributed data processing environment 100, such as the one depicted in FIG. 1, in accordance with an embodiment of the present invention. In an embodiment, setup module 124 of preventative workplace injury alert program 122 completes a one-time setup with a user. The one-time setup allows for setup module 124 of preventative workplace injury alert program 122 to capture relevant information about the user to create a user profile and register a user computing device with preventative workplace injury alert program 122. It should be appreciated that the process depicted in FIG. 2 illustrates one possible iteration of setup module 124 of preventative workplace injury alert program 122, which may be repeated for each opt-in request received by setup module 124 of preventative workplace injury alert program 122.

In step 210, setup module 124 of preventative workplace injury alert program 122 receives a request from a user to opt-in. A user may include, but is not limited to, a worker engaged in the fabrication, assembly, material handling, warehousing and shipping of new products either from raw materials or by assembling different components through physical, chemical, or mechanical means, as well as a worker engaged in the maintenance, repair, and other closely related activities to those previously listed. In an embodiment, setup module 124 of preventative workplace injury alert program 122 receives a request from a user to opt-in to preventative workplace injury alert program 122. In an embodiment, setup module 124 of preventative workplace injury alert program 122 receives a request from a user to opt-in to preventative workplace injury alert program 122 through user interface 132 of user computing device 130. By opting-in, the user agrees to share data with observational movement activity corpus 128.

In step 220, setup module 124 of preventative workplace injury alert program 122 requests information from the user. In an embodiment, responsive to receiving a request from a user to opt-in, setup module 124 of preventative workplace injury alert program 122 requests information from the user. In an embodiment, setup module 124 of preventative workplace injury alert program 122 requests information from the user to create a user profile. In an embodiment, setup module 124 of preventative workplace injury alert program 122 requests information from the user through user interface 132 of user computing device 130. Information requested from the user includes, but is not limited to, information about user preferences (e.g., general user system settings such as alert notifications for user computing device 130); information about alert notification preferences (e.g., alert notification preview, alert notification style (i.e., alert notification appearing on lock screen, notification center, and/or banner; alert notification appearing temporary or persistently; alert notification sound on or off; alert notification grouping automatically, by application, or off), and alert notification frequency); information necessary to create a user profile (e.g., information about the user's primary job, information about the user's primary job functions, information about the user (e.g., age), information about the user's medical history (e.g., prior history of knee, arm, or back pain), information about the user's assistive devices needed to perform user's primary job, and information about the user's wearable devices worn when performing user's primary job).

In step 230, setup module 124 of preventative workplace injury alert program 122 receives the requested information from the user. In an embodiment, responsive to requesting information from the user, setup module 124 of preventative workplace injury alert program 122 receives the requested information from the user. In an embodiment, setup module 124 of preventative workplace injury alert program 122 receives the requested information from the user through user interface 132 of user computing device 130.

In step 240, setup module 124 of preventative workplace injury alert program 122 creates a user profile. In an embodiment, responsive to receiving the requested information from the user, setup module 124 of preventative workplace injury alert program 122 creates a user profile. In an embodiment, setup module 124 of preventative workplace injury alert program 122 creates a user profile for the user. In an embodiment, setup module 124 of preventative workplace injury alert program 122 creates a user profile with information input by the user during setup regarding the user (i.e., information necessary to create a user profile) as well as user preferences and alert notification preferences.

In step 250, setup module 124 of preventative workplace injury alert program 122 stores the user profile. In an embodiment, responsive to creating a user profile, setup module 124 of preventative workplace injury alert program 122 stores the user profile. In an embodiment, setup module 124 of preventative workplace injury alert program 122 stores the user profile in a database, e.g., observational movement activity corpus 128.

In step 260, setup module 124 of preventative workplace injury alert program 122 enables the user to register user computing device 130. In an embodiment, responsive to storing the user profile, setup module 124 of preventative workplace injury alert program 122 enables the user to register user computing device 130. In an embodiment, setup module 124 of preventative workplace injury alert program 122 enables the user to register user computing device 130 through user interface 132. In an embodiment, setup module 124 of preventative workplace injury alert program 122 requests permission to monitor the body movement and the posture of the user during a defined period of time (e.g., during a work shift) through user computing device 130. In an embodiment, setup module 124 of preventative workplace injury alert program 122 requests permission to gather sensor data on the body movement and the posture of the user during a defined period of time through user computing device 130. In an embodiment, setup module 124 of preventative workplace injury alert program 122 requests permission to capture one or more photographs of the user to monitor the body movement and the posture of the user during a defined period of time (e.g., during a work shift) through camera 140. In an embodiment, setup module 124 of preventative workplace injury alert program 122 requests permission from the user through user computing device 130. In an embodiment, setup module 124 of preventative workplace injury alert program 122 enables the user to grant permission through user interface 132 of user computing device 130.

Figure 3:
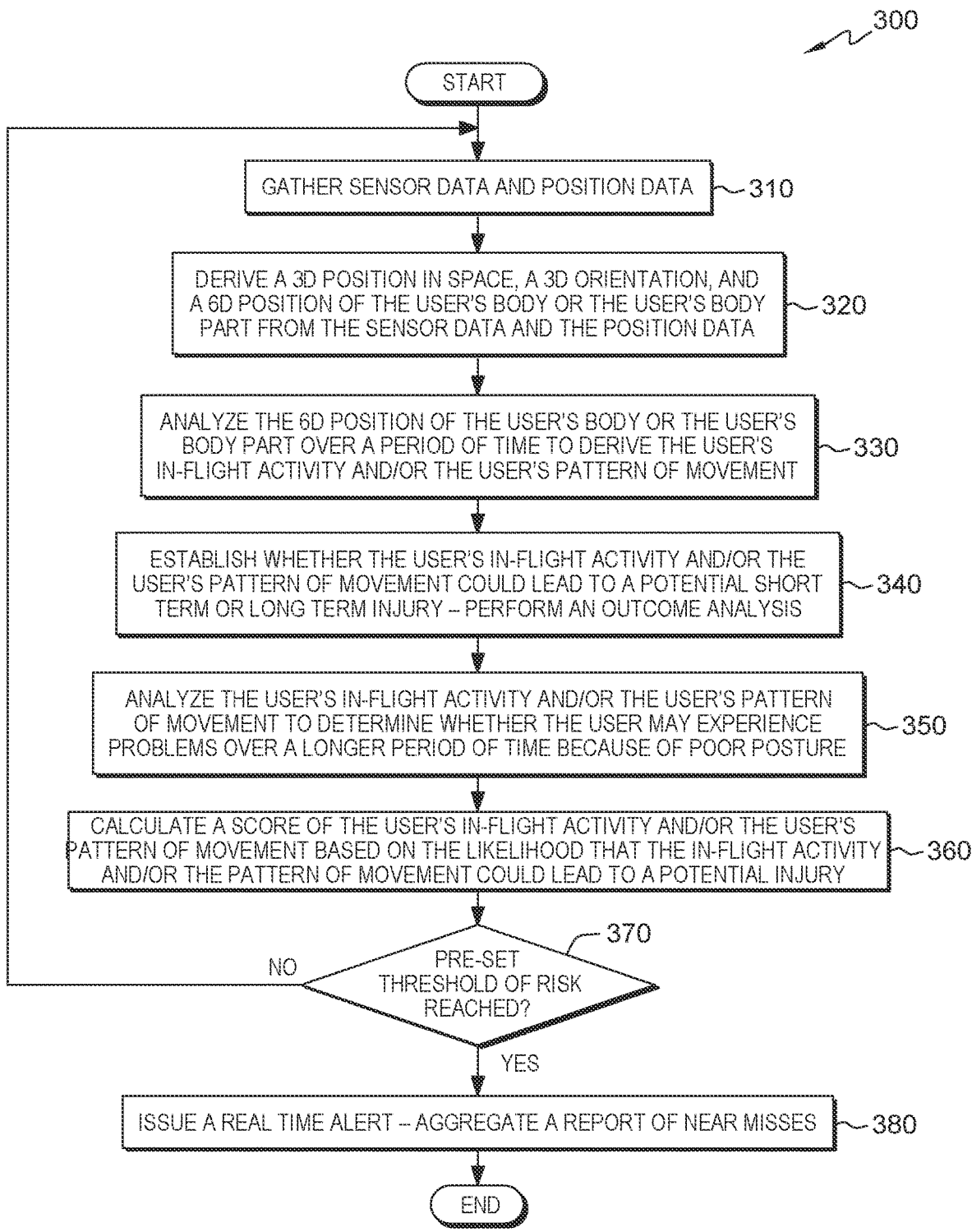
FIG. 3 is a flowchart illustrating the operational steps of the preventative workplace injury alert program, on the server within the distributed data processing environment of FIG. 1, in accordance with an embodiment of the present invention.

FIG. 3 is a flowchart, generally designated 300, illustrating the operational steps of preventative workplace injury alert program 122, on server 120 within distributed data processing environment 100 of FIG. 1, in accordance with an embodiment of the present invention. In an embodiment, preventative workplace injury alert program 122 operates to gather sensor data on the movement and the posture of the body of the user from user computing device 130 and position data from one or more photographs taken of the user using CNN pose estimation 142; to derive the precise 6D position of the user's body or the user's body part from the sensor data and the position data; to derive the user's in-flight activity and the user's pattern of movement from the 6D position of the user's body or the user's body part; to produce a personalized and aggregate movement outcome analysis and posture analysis as well as an analyzed exertion outcome detailing the potential results of a workplace injury because of the user's in-flight activity and/or the user's pattern of movement; and to issue a real time alert to warn the user of an in-flight activity or a pattern of movement that could lead to a potential short-term or long-term injury. It should be appreciated that the process depicted in FIG. 3 illustrates one possible iteration of the process flow, which may be repeated continually during each defined period of time that preventative workplace injury alert program 122 received permission from the user to monitor the body movement and the posture of the user.

In step 310, preventative workplace injury alert program 122 gathers sensor data and position data.

In an embodiment, preventative workplace injury alert program 122 monitors the movement and the posture of the user's body during a defined period of time. In an embodiment, preventative workplace injury alert program 122 monitors the movement and the posture of the user's body through an application of micro-location analysis enabled by a mesh network of 5G sensors.

In an embodiment, preventative workplace injury alert program 122 gathers sensor data on the movement and the posture of the user's body during the defined period of time. In an embodiment, preventative workplace injury alert program 122 gathers sensor data collected by user computing device 130. In an embodiment, preventative workplace injury alert program 122 stores the sensor data in a database, e.g., observational movement activity corpus 128.

In an embodiment, preventative workplace injury alert program 122 gathers position data of the user's body during the defined period of time. In an embodiment, preventative workplace injury alert program 122 gathers position data from one or more photographs captured of the user's body (i.e., through camera 140) using CNN pose estimation 142. In an embodiment, preventative workplace injury alert program 122 stores the position data from the one or more photographs of the user in a database, e.g., observational movement activity corpus 128.

In step 320, mmWAVE 5G positional localization 6D positioning module 125 of preventative workplace injury alert program 122 derives a 3D position in space, a 3D orientation, and a 6D position of the user's body from the sensor data and the position data gathered. In an embodiment, responsive to gathering the sensor data and the position data, mmWAVE 5G positional localization 6D positioning module 125 of preventative workplace injury alert program 122 derives a 3D position in space, a 3D orientation, and a 6D position of the user's body from the sensor data and the position data gathered.

In an embodiment, mmWAVE 5G positional localization 6D positioning module 125 of preventative workplace injury alert program 122 derives the 3D position in space of the user's body or, more specifically, the user's body part from the sensor data and the position data gathered. The 3D position in space of the user's body or the user's body part is the position of the user's body or the user's body part in a given location as it relates to its specific location in space. In an embodiment, preventative workplace injury alert program 122 stores the 3D position in space of the user's body or the user's body part in a database, e.g., observational movement activity corpus 128. For example, mmWAVE 5G positional localization 6D positioning module 125 of preventative workplace injury alert program 122 derives the precise location of where the user is standing. In another example, mmWAVE 5G positional localization 6D positioning module 125 of preventative workplace injury alert program 122 derives how low the user is crouching to the ground.

In an embodiment, mmWAVE 5G positional localization 6D positioning module 125 of preventative workplace injury alert program 122 derives the 3D orientation of the user's body or the user's body part from the sensor data and the position data gathered. In an embodiment, preventative workplace injury alert program 122 stores the 3D orientation of the user's body or the user's body part in a database, e.g., observational movement activity corpus 128. For example, mmWAVE 5G positional localization 6D positioning module 125 of preventative workplace injury alert program 122 derives the precise angle of the user's back as the user is bending down.

In an embodiment, mmWAVE 5G positional localization 6D positioning module 125 of preventative workplace injury alert program 122 derives the precise 6D position of the user's body or the user's body part from the sensor data and the position data gathered. In an embodiment, mmWAVE 5G positional localization 6D positioning module 125 of preventative workplace injury alert program 122 stores the 6D position of the user's body or the user's body part in a database, e.g., observational movement activity corpus 128. In an embodiment, mmWAVE 5G positional localization 6D positioning module 125 of preventative workplace injury alert program 122 gathers identifying data of the user from the user profile. In an embodiment, mmWAVE 5G positional localization 6D positioning module 125 of preventative workplace injury alert program 122 stores the identifying data of the user with the 6D position of the user's body or the user's body part in a database, e.g., observational movement activity corpus 128.

In step 330, mmWAVE 5G positional localization 6D positioning module 125 of preventative workplace injury alert program 122 analyzes the 6D position of the user's body or the user's body part during the defined period of time. In an embodiment, responsive to deriving the 3D position in space, the 3D orientation, and the 6D position of the user's body from the sensor data and the position data gathered, mmWAVE 5G positional localization 6D positioning module 125 of preventative workplace injury alert program 122 analyzes the 6D position of the user's body or the user's body part during the defined period of time. In an embodiment, mmWAVE 5G positional localization 6D positioning module 125 of preventative workplace injury alert program 122 analyzes the 6D position of the user's body or the user's body part to derive the user's in-flight activity. In an embodiment, mmWAVE 5G positional localization 6D positioning module 125 of preventative workplace injury alert program 122 analyzes the 6D position of the user's body or the user's body part to derive the user's pattern of movement. In an embodiment, preventative workplace injury alert program 122 stores the user's in-flight activity in a database, e.g., observational movement activity corpus 128. In an embodiment, preventative workplace injury alert program 122 stores the user's pattern of movement in a database, e.g., observational movement activity corpus 128.

For example, mmWAVE 5G positional localization 6D positioning module 125 of preventative workplace injury alert program 122 analyzes the 6D position of the user's body and finds that over the course of a 3 second period of time the user performs a bending motion. The bending motion is implied from the orientation of the user's lower back, the position of the user's knees, and the lowering of the user's arms.

In step 340, preventative workplace injury alert program 122 determines whether the user's in-flight activity and/or the user's pattern of movement can result in a potential short-term or long-term injury. In an embodiment, responsive to analyzing the 6D position of the user's body or the user's body part during the defined period of time, preventative workplace injury alert program 122 determines whether the user's in-flight activity and/or the user's pattern of movement can result in a potential short-term or long-term injury. In an embodiment, preventative workplace injury alert program 122 determines whether the user's in-flight activity and/or the user's pattern of movement can result in a potential short-term or long-term injury based on prior instances of similar in-flight activities or patterns of movement of the user.

In an embodiment, preventative workplace injury alert program 122 retrieves prior instances of similar in-flight activities or patterns of movement of the user from the database, e.g., observational movement activity corpus 128. In an embodiment, preventative workplace injury alert program 122 retrieves prior instances of similar in-flight activities or patterns of movement of other users of preventative workplace injury alert program 122 from the database, e.g., observational movement activity corpus 128. In an embodiment, preventative workplace injury alert program 122 retrieves any known outcomes of the prior instances of the similar in-flight activities from the database, e.g., observational movement activity corpus 128.

For example, preventative workplace injury alert program 122 finds that the user was extending the user's arm to reach an item on a high shelf. Preventative workplace injury alert program 122 retrieves prior instances of similar in-flight activities of the user from observational movement activity corpus 128. Preventative workplace injury alert program 122 also retrieves any known outcomes of the prior instances of the similar in-flight activities.

In an embodiment, preventative workplace injury alert program 122 compares the user's in-flight activity and/or the user's pattern of movement to the prior instances of similar in-flight activities and/or patterns of movement of the user from the database, i.e., observational movement activity corpus 128.

In an embodiment, preventative workplace injury alert program 122 performs an outcome analysis based on the user's current in-flight activity and/or pattern of movement and the user's prior in-flight activity and/or pattern of movement. In an embodiment, preventative workplace injury alert program 122 calculates the one or more possible paths of the user. When calculating the one or more possible paths of the user, F represents the set of all possible paths the user can take. Within the set of all possible paths, there exists a subset, F1, F2, and F3. The subset represents the possible subparts of movements (e.g., the possible subsets of all paths of a user's left arm or the possible subsets of all paths of the user's right leg). Each possible path of the set of all possible paths is represented as cartesian coordinates (i.e., F={x, y, z in R, T}) in space and time. A threshold is pre-set at e>0. If the user's current in-flight activity and/or the user's pattern of movement is within the pre-set threshold of the user's prior in-flight activity and/or pattern of movement, then preventative workplace injury alert program 122 can predict the likelihood of a short-term injury or a long-term injury resulting. For example, if a path (Fn) is outside the pre-set threshold of historical paths (F1, F2, F3, F4), then preventative workplace injury alert program 122 assumes that there is a low chance of injury. However, if a path (Fn) is within the pre-set threshold of historical paths (F1, F2, F3, F4), then preventative workplace injury alert program 122 assumes that there is a high chance of injury. In another embodiment, preventative workplace injury alert program 122 performs the outcome analysis on anonymized aggregate in-flight data. For example, preventative workplace injury alert program 122 determines whether a particular in-flight activity led to an injury or complaint in the aggregate even if not for the user.

In step 350, posture analysis module 126 of preventative workplace injury alert program 122 analyzes the user's in-flight activity to determine whether the user may experience problems over a longer period of time because of poor posture. In an embodiment, responsive to determining whether the user's in-flight activity and/or the user's pattern of movement can result in a potential short-term or long-term injury, posture analysis module 126 of preventative workplace injury alert program 122 analyzes the user's in-flight activity to determine whether the user may experience problems over a longer period of time because of poor posture.

For example, in step 340, preventative workplace injury alert program 122 derives the user's in-flight activity to determine the position of the user's back as the user is seated at a desk. Preventative workplace injury alert program 122 finds that the user sits hunched over while seated at the desk. Posture analysis module 126 of preventative workplace injury alert program 122 analyzes the user's in-flight activity and determines that over time the user's suboptimal posture may lead to long-term back injuries.

In step 360, injury analysis module 127 of preventative workplace injury alert program 122 calculates a score of the user's in-flight activity and pattern of movement. In an embodiment, responsive to analyzing the user's in-flight activity to determine whether the user may experience problems over a longer period of time because of poor posture, injury analysis module 127 of preventative workplace injury alert program 122 calculates a score of the user's in-flight activity and pattern of movement. In an embodiment, injury analysis module 127 of preventative workplace injury alert program 122 calculates a score of the user's in-flight activity and pattern of movement based on the likelihood that the in-flight activity and the pattern of movement could lead to a potential short-term or long-term injury. In an embodiment, injury analysis module 127 of preventative workplace injury alert program 122 considers the user's medical history when calculating a score of the user's in-flight activity and pattern of movement. For example, injury analysis module 127 of preventative workplace injury alert program 122 considers the user's history of back pain if the user is bending down to lift an item. In an embodiment, injury analysis module 127 of preventative workplace injury alert program 122 considers the situational analysis of the user's in-flight activity and pattern of movement when calculating a score of the user's in-flight activity and pattern of movement. For example, injury analysis module 127 of preventative workplace injury alert program 122 considers the estimated weight of an item being picked up by the user when calculating a score of the user's in-flight activity and pattern of movement.

In an embodiment, preventative workplace injury alert program 122 categorizes the user's in-flight activity and pattern of movement. In an embodiment, preventative workplace injury alert program 122 categorizes the user's in-flight activity and pattern of movement based on the calculated score. In an embodiment, preventative workplace injury alert program 122 categorizes the user's in-flight activity and pattern of movement as a high-risk situation, a medium-risk situation, or a low-risk situation.

In decision 370, preventative workplace injury alert program 122 determines whether a pre-set threshold of risk has been reached. In an embodiment, responsive to injury analysis module 127 of preventative workplace injury alert program 122 calculating the score of the user's in-flight activity and pattern of movement, preventative workplace injury alert program 122 determines whether a pre-set threshold of risk has been reached. In an embodiment, preventative workplace injury alert program 122 determines the pre-set threshold of risk has been reached based on the score calculated in step 360. In an embodiment, preventative workplace injury alert program 122 determines the pre-set threshold of risk has been reached when injury analysis module 127 of preventative workplace injury alert program 122 scores the user's in-flight activity at a confidence level beyond the pre-set threshold of risk. If preventative workplace injury alert program 122 determines the pre-set threshold of risk has been reached (decision 370, YES branch), then preventative workplace injury alert program 122 proceeds to step 380, issuing a real-time alert. If preventative workplace injury alert program 122 determines the pre-set threshold of risk has not been reached (decision 370, NO branch), then preventative workplace injury alert program 122 returns to step 310, gathering the sensor data and the position data.

In step 380, preventative workplace injury alert program 122 issues a real time alert. In an embodiment, responsive to determining the pre-set threshold of risk has been reached, preventative workplace injury alert program 122 issues a real time alert. In an embodiment, preventative workplace injury alert program 122 issues a real time alert to warn the user of the user's in-flight activity or pattern of movement that can lead to a potential short-term and/or long-term injuries. In an embodiment, preventative workplace injury alert program 122 issues a real time alert including, but not limited to, information such as the user's in-flight activity or pattern of movement, the potential short-term and/or long-term injury risks of performing the user's in-flight activity or pattern of movement, and the recommended posture with which to perform the user's in-flight activity or pattern of movement. In an embodiment, preventative workplace injury alert program 122 issues a real time alert as an alert notification. In an embodiment, preventative workplace injury alert program 122 issues a real time alert as an alert notification on user interface 132 of user computing device 130.

In an embodiment, preventative workplace injury alert program 122 issues a real time alert based on the level of risk of the user's in-flight activity or pattern of movement. The level of risk of the user's in-flight activity or pattern of movement (i.e., a high-risk situation, a medium-risk situation, or a low-risk situation) is determined based on the score calculated in step 360. In an embodiment, preventative workplace injury alert program 122 issues a real time alert, in a high-risk situation, through a myriad of notification methods including, but not limited to, an alarm, a buzzing, and a haptic feedback alert sent to the user through user computing device 130 and/or to people in direct proximity to the user. For example, in a high-risk situation, preventative workplace injury alert program 122 issues a real time alert over a PA system for the user as well as the people in direct proximity to the user to hear. In another embodiment, preventative workplace injury alert program 122 issues a real time alert, in a medium-risk situation, through a myriad of less aggressive notification methods than the high-risk situation including, but not limited to, an alarm sounding at a lower volume, a buzz that is less prolonged, and a haptic feedback alert sent to the user through user computing device 130. In another embodiment, preventative workplace injury alert program 122 issues a real time alert, in a low-risk situation, in a casual notification method such as a ping sent to the user through user computing device 130.

In an embodiment, preventative workplace injury alert program 122 stores the real time alert in a database, e.g., observational movement activity corpus 128.

In an embodiment, preventative workplace injury alert program 122 aggregates a report of near misses. Near misses are events when the user was notified to stop doing an in-flight activity or a pattern of movement. The report of near misses includes, but is not limited to, all data elements related to a specific point in time of a near miss (e.g., biometrics and video feed of an incidence). In an embodiment, preventative workplace injury alert program 122 aggregates the report of near misses to provide insight to the user into the in-flight activities and patterns of movement that are more prone to injury. In an embodiment, preventative workplace injury alert program 122 uses k-means, or any other form of clustering, to demonstrate the in-flight activities and patterns of movement causing the most concern, so that the user can optimally prevent future injuries. In an embodiment, preventative workplace injury alert program 122 sends the report of near misses to the user through user interface 132 of user computing device 130. In an embodiment, preventative workplace injury alert program 122 stores the report of near misses in a database, e.g., observational movement activity corpus 128.

Figure 4:
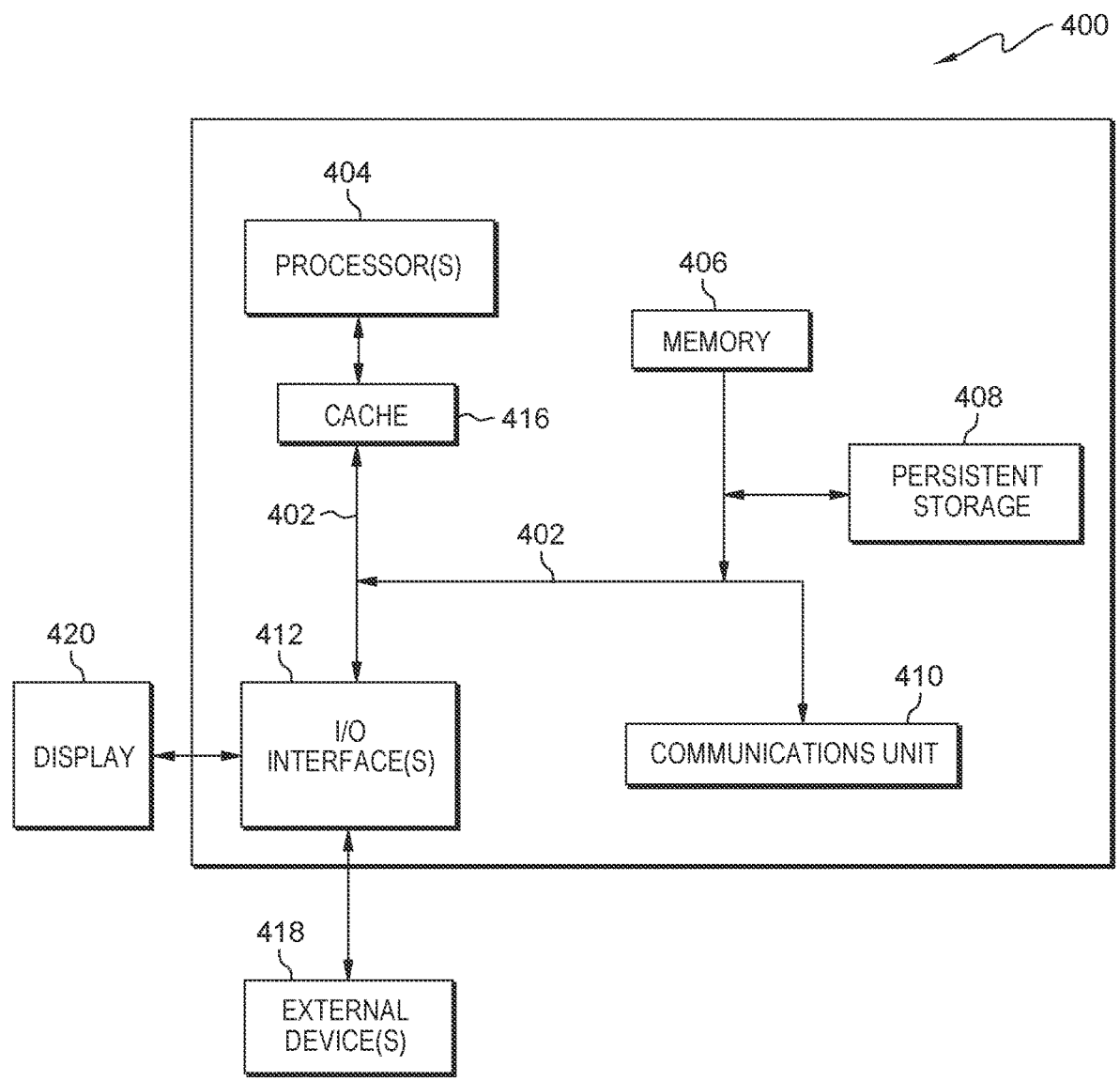
FIG. 4 is a block diagram illustrating the components of a computing device within the distributed data processing environment of FIG. 1, in accordance with an embodiment of the present invention.

FIG. 4 is a block diagram illustrating the components of computing device 400 within distributed data processing environment 100 of FIG. 1, in accordance with an embodiment of the present invention. It should be appreciated that FIG. 4 provides only an illustration of one implementation and does not imply any limitations with regard to the environments in which different embodiments can be implemented. Many modifications to the depicted environment can be made.

Computing device 400 includes processor(s) 404, memory 406, cache 416, communications fabric 402, persistent storage 408, input/output (I/O) interface(s) 412, and communications unit 410. Communications fabric 402 provides communications between memory 406, cache 416, persistent storage 408, input/output (I/O) interface(s) 412, and communications unit 410. Communications fabric 402 can be implemented with any architecture designed for passing data and/or control information between processors (such as microprocessors, communications and network processors, etc.), system memory, peripheral devices, and any other hardware components within a system. For example, communications fabric 402 can be implemented with one or more buses or a cross switch. Memory 406 and persistent storage 408 are computer readable storage media. In this embodiment, memory 406 includes random access memory (RAM). In general, memory 406 can include any suitable volatile or non-volatile computer readable storage media. Cache 416 is a fast memory that enhances the performance of computer processor(s) 404 by holding recently accessed data, and data near accessed data, from memory 406.

Program instructions and data (e.g., software and data) used to practice embodiments of the present invention may be stored in persistent storage 408 and in memory 406 for execution by one or more of the respective processor(s) 404 via cache 416. In an embodiment, persistent storage 408 includes a magnetic hard disk drive. Alternatively, or in addition to a magnetic hard disk drive, persistent storage 408 can include a solid-state hard drive, a semiconductor storage device, a read-only memory (ROM), an erasable programmable read-only memory (EPROM), a flash memory, or any other computer readable storage media that is capable of storing program instructions or digital information.

The media used by persistent storage 408 may also be removable. For example, a removable hard drive may be used for persistent storage 408. Other examples include optical and magnetic disks, thumb drives, and smart cards that are inserted into a drive for transfer onto another computer readable storage medium that is also part of persistent storage 408. Software and data can be stored in persistent storage 408 for access and/or execution by one or more of the respective processor(s) 404 via cache 416. With respect to user computing device 130, software and data includes user interface 132. With respect to server 120, software and data includes preventative workplace injury alert program 122.

Communications unit 410, in these examples, provides for communications with other data processing systems or devices. In these examples, communications unit 410 includes one or more network interface cards. Communications unit 410 may provide communications through the use of either or both physical and wireless communications links. Program instructions and data (e.g., software and data) used to practice embodiments of the present invention may be downloaded to persistent storage 408 through communications unit 410.

I/O interface(s) 412 allows for input and output of data with other devices that may be connected to each computer system. For example, I/O interface(s) 412 may provide a connection to external device(s) 418, such as a keyboard, a keypad, a touch screen, and/or some other suitable input device. External device(s) 418 can also include portable computer readable storage media, such as, for example, thumb drives, portable optical or magnetic disks, and memory cards. Program instructions and data (e.g., software and data) used to practice embodiments of the present invention can be stored on such portable computer readable storage media and can be loaded onto persistent storage 408 via I/O interface(s) 412. I/O interface(s) 412 also connect to display 420.

Display 420 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

While particular embodiments of the present invention have been shown and described here, it will be understood to those skilled in the art that, based upon the teachings herein, changes and modifications may be made without departing from the embodiments and its broader aspects. Therefore, the appended claims are to encompass within their scope all such changes and modifications as are within the true spirit and scope of the embodiments. Furthermore, it is to be understood that the embodiments are solely defined by the appended claims. It will be understood by those with skill in the art that if a specific number of an introduced claim element is intended, such intent will be explicitly recited in the claim, and in the absence of such recitation no such limitation is present. For a non-limiting example, as an aid to understand, the following appended claims contain usage of the introductory phrases "at least one" and "one or more" to introduce claim elements. However, the use of such phrases should not be construed to imply that the introduction of a claim element by the indefinite articles "a" or "an" limits any particular claim containing such introduced claim element to embodiments containing only one such element, even when the same claim includes the introductory phrases "at least one" or "one or more" and indefinite articles such as "a" or "an", the same holds true for the use in the claims of definite articles.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart illustrations and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart illustrations and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart illustrations and/or block diagram block or blocks.

The flowchart illustrations and block diagrams in the Figures illustrate the architecture, functionality, and operation of possible implementations of systems, methods, and computer program products according to various embodiments of the present invention. In this regard, each block in the flowchart illustrations or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each flowchart illustration and/or block of the block diagrams, and combinations of flowchart illustration and/or blocks in the block diagrams, can be implemented by special purpose hardware-based systems that perform the specified functions or acts or carry out combinations of special purpose hardware and computer instructions.

The descriptions of the various embodiments of the present invention have been presented for purposes of illustration but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A computer-implemented method comprising:
    monitoring, by one or more processors, a body movement and a posture of a user through an application of micro-location analysis by utilizing a mesh network of 5G sensors over a period of time;
    determining, by the one or more processors, whether the body movement and the posture detected can lead to an activity or a series of activities that can result in a potential injury, wherein determining whether the body movement and the posture detected can lead to the activity or the series of activities that can result in the potential injury comprises:
        deriving, by the one or more processors, a three-dimensional position in space of the user from the sensor data and the position data;

deriving, by the one or more processors, a three-dimensional orientation of the user from the sensor data and the position data;
deriving, by the one or more processors, a six-dimensional position of the user from the three-dimensional position in space and the three-dimensional orientation of the user; and
analyzing, by the one or more processors, the six-dimensional position of the user to derive an in-flight activity and a pattern of movement of the user; and
responsive to determining a pre-set threshold of risk has been reached, issuing, by the one or more processors, a real time alert to the user to warn of the potential injury.

2. The computer-implemented method of claim 1, wherein monitoring the body movement and the posture of the user through the application of micro-location analysis by utilizing the mesh network of 5G sensors over the period of time further comprises:
gathering, by the one or more processors, sensor data on the body movement and the posture of the user from a user computing device;
capturing, by the one or more processors, one or more photographs of the body movement and the posture of the user through a camera; and
gathering, by the one or more processors, position data from the one or more photographs of the body movement and the posture using a convolutional neural network.

3. The computer-implemented method of claim 1, wherein determining whether the body movement and the posture detected can lead to the activity or the series of activities that can result in the potential injury further comprises:
comparing, by the one or more processors, the in-flight activity and the pattern of movement of the user to one or more prior instances of in-flight activities and patterns of movement;
performing, by the one or more processors, an outcome analysis on the in-flight activity and the pattern of movement of the user based on a comparison;
calculating, by the one or more processors, a score of the in-flight activity and the pattern of movement of the user based on the likelihood that the in-flight activity and the pattern of movement could lead to the potential injury;
categorizing, by the one or more processors, the in-flight activity and the pattern of movement of the user based on a risk of an immediate potential injury or a long term potential injury; and
determining, by the one or more processors, whether the pre-set threshold of risk has been reached based on the score of the in-flight activity and the pattern of movement of the user.

4. The computer-implemented method of claim 3, wherein performing the outcome analysis on the in-flight activity and the pattern of movement of the user further comprises:
calculating, by the one or more processors, one or more possible paths of the user;
determining, by the one or more processors, the one or more possible paths of the user are within a threshold of one or more historical paths; and
predicting, by the one or more processors, a possibility the potential injury will occur.

5. The computer-implemented method of claim 3, wherein calculating the score of the in-flight activity and the pattern of movement of the user based on the likelihood that the in-flight activity and the pattern of movement could lead to the potential injury further comprises:
analyzing, by the one or more processors, a medical history of the user; and
performing, by the one or more processors, a situational analysis of the in-flight activity and the pattern of movement of the user.

6. The computer-implemented method of claim 1, wherein the real time alert includes the in-flight activity and the pattern of movement of the user, the potential injury, and a recommended posture to perform the in-flight activity and the pattern of movement of the user.

7. The computer-implemented method of claim 1, wherein the real time alert is issued based on a level of risk of the in-flight activity and the pattern of movement of the user.

8. The computer-implemented method of claim 7, wherein the level of risk is determined based on the score calculated of the in-flight activity and the pattern of movement of the user.

9. The computer-implemented method of claim 7, wherein:
the level of risk is a high-risk situation, a medium-risk situation, or a low-risk situation;
in the high-risk situation, the real time alert is issued through a myriad of notification methods including an alarm, a buzzing, and a haptic feedback alert sent to the user and to one or more people in direct proximity of the user;
in the medium-risk situation, the real time alert is issued through a myriad of less aggressive notification methods including an alarm sounding at a lower volume, a buzz that is less prolonged, and a haptic feedback alert sent to the user; and
in the low-risk situation, the real time alert is issued through a casual notification method such as a ping sent to the user.

10. A computer program product comprising:
one or more computer readable storage media and program instructions stored on the one or more computer readable storage media, the program instructions comprising:
program instructions to monitor a body movement and a posture of a user through an application of micro-location analysis enabled by a mesh network of 5G sensors over a period of time;
program instructions to determine whether the body movement and the posture detected can lead to an activity or a series of activities that can result in a potential injury, wherein determining whether the body movement and the posture detected can lead to the activity or the series of activities that can result in the potential injury comprises:
program instructions to derive, by the one or more processors, a three-dimensional position in space of the user from the sensor data and the position data;
program instructions to derive, by the one or more processors, a three-dimensional orientation of the user from the sensor data and the position data;
program instructions to derive, by the one or more processors, a six-dimensional position of the user from the three-dimensional position in space and the three-dimensional orientation of the user; and program instructions to analyze, by the one or more processors, the six-dimensional position of the user to derive an in-flight activity and a pattern of movement of the user; and responsive to determining a pre-set threshold of risk has been reached, program instructions to issue a real time alert to the user to warn of the potential injury.

11. The computer program product of claim 10, wherein monitoring the body movement and the posture of the user through the application of micro-location analysis enabled by the mesh network of 5G sensors over the period of time further comprises:

program instructions to gather sensor data on the body movement and the posture of the user from a user computing device;

program instructions to capture one or more photographs of the body movement and the posture of the user through a camera; and program instructions to gather position data from the one or more photographs of the body movement and the posture using a convolutional neural network.

12. The computer program product of claim 10, wherein determining whether the body movement and the posture detected can lead to the activity or the series of activities that can result in the potential injury further comprises:

program instructions to compare the in-flight activity and the pattern of movement of the user to one or more prior instances of in-flight activities and patterns of movement;

program instructions to perform an outcome analysis on the in-flight activity and the pattern of movement of the user based on a comparison;

program instructions to calculate a score of the in-flight activity and the pattern of movement of the user based on the likelihood that the in-flight activity and the pattern of movement could lead to the potential injury;

program instructions to categorize the in-flight activity and the pattern of movement of the user based on a risk of an immediate potential injury or a long term potential injury; and program instructions to determine whether the pre-set threshold of risk has been reached based on the score of the in-flight activity and the pattern of movement of the user.

13. The computer program product of claim 12, wherein performing the outcome analysis on the in-flight activity and the pattern of movement of the user further comprises:

program instructions to calculate one or more possible paths of the user;

program instructions to determine the one or more possible paths of the user are within a threshold of one or more historical paths; and program instructions to predict a possibility the potential injury will occur.

14. The computer program product of claim 12, wherein calculating the score of the in-flight activity and the pattern of movement of the user based on the likelihood that the in-flight activity and the pattern of movement could lead to the potential injury further comprises:

program instructions to analyze a medical history of the user; and program instructions to perform a situational analysis of the in-flight activity and the pattern of movement of the user.

15. The computer program product of claim 10, wherein the real time alert includes the in-flight activity and the pattern of movement of the user, the potential injury, and a recommended posture to perform the in-flight activity and the pattern of movement of the user.

16. A computer system comprising:
one or more computer processors;
one or more computer readable storage media;
program instructions collectively stored on the one or more computer readable storage media for execution by at least one of the one or more computer processors, the stored program instructions comprising:
program instructions to monitor a body movement and a posture of a user through an application of micro-location analysis enabled by a mesh network of 5G sensors over a period of time;
program instructions to determine whether the body movement and the posture detected can lead to an activity or a series of activities that can result in a potential injury, wherein determining whether the body movement and the posture detected can lead to the activity or the series of activities that can result in the potential injury comprises:
program instructions to derive, by the one or more processors, a three-dimensional position in space of the user from the sensor data and the position data;
program instructions to derive, by the one or more processors, a three-dimensional orientation of the user from the sensor data and the position data;
program instructions to derive, by the one or more processors, a six-dimensional position of the user from the three-dimensional position in space and the three-dimensional orientation of the user;
program instructions to analyze, by the one or more processors, the six-dimensional position of the user to derive an in-flight activity and a pattern of movement of the user;
program instructions to compare, by the one or more processors, the in-flight activity and the pattern of movement of the user to one or more prior instances of in-flight activities and patterns of movement; and
program instructions to perform, by the one or more processors, an outcome analysis on the in-flight activity and the pattern of movement of the user based on a comparison; and
responsive to determining a pre-set threshold of risk has been reached, program instructions to issue a real time alert to the user to warn of the potential injury.

17. The computer system of claim 16, wherein monitoring the body movement and the posture of the user through the application of micro-location analysis enabled by the mesh network of 5G sensors over the period of time further comprises:

program instructions to gather sensor data on the body movement and the posture of the user from a user computing device;

program instructions to capture one or more photographs of the body movement and the posture of the user through a camera; and program instructions to gather position data from the one or more photographs of the body movement and the posture using a convolutional neural network.

18. The computer system of claim 16, wherein determining whether the body movement and the posture detected can lead to the activity or the series of activities that can result in the potential injury further comprises:

program instructions to calculate a score of the in-flight activity and the pattern of movement of the user based on the likelihood that the in-flight activity and the pattern of movement could lead to the potential injury;

program instructions to categorize the in-flight activity and the pattern of movement of the user based on a risk of an immediate potential injury or a long term potential injury; and program instructions to determine whether the pre-set threshold of risk has been reached based on the score of the in-flight activity and the pattern of movement of the user.

19. The computer system of claim 18, wherein performing the outcome analysis on the in-flight activity and the pattern of movement of the user further comprises:

program instructions to calculate one or more possible paths of the user;

program instructions to determine the one or more possible paths of the user are within a threshold of one or more historical paths; and program instructions to predict a possibility the potential injury will occur.

20. The computer system of claim 18, wherein calculating the score of the in-flight activity and the pattern of movement of the user based on the likelihood that the in-flight activity and the pattern of movement could lead to the potential injury further comprises:

program instructions to analyze a medical history of the user; and program instructions to perform a situational analysis of the in-flight activity and the pattern of movement of the user.

* * * * *